US009023875B2

(12) United States Patent
Luesch et al.

(10) Patent No.: US 9,023,875 B2
(45) Date of Patent: *May 5, 2015

(54) MACROCYCLIC COMPOUNDS AND METHODS OF TREATMENT

(71) Applicant: University of Florida Research Foundation, Inc., Gainesville, FL (US)

(72) Inventors: Hendrik Luesch, Gainesville, FL (US); Taori Kanchan, Gainesville, FL (US); Valerie J. Paul, Fort Pierce, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,044

(22) Filed: Jan. 22, 2013

(65) Prior Publication Data
US 2014/0031400 A1 Jan. 30, 2014

Related U.S. Application Data

(60) Continuation of application No. 13/331,497, filed on Dec. 20, 2011, now Pat. No. 8,357,708, which is a division of application No. 12/677,078, filed as application No. PCT/US2008/010633 on Sep. 9, 2008, now Pat. No. 8,129,418.

(60) Provisional application No. 60/970,986, filed on Sep. 9, 2007, provisional application No. 61/009,903, filed on Jan. 3, 2008, provisional application No. 61/030,993, filed on Feb. 24, 2008, provisional application No. 61/125,542, filed on Apr. 24, 2008, provisional application No. 61/189,093, filed on Aug. 15, 2008.

(51) Int. Cl.
| | |
|---|---|
| *A61K 31/429* | (2006.01) |
| *C07D 513/14* | (2006.01) |
| *C07D 513/18* | (2006.01) |
| *A61K 45/06* | (2006.01) |
| *A61K 38/00* | (2006.01) |

(52) U.S. Cl.
CPC .............. *C07D 513/14* (2013.01); *A61K 38/00* (2013.01); *C07D 513/18* (2013.01); *A61K 31/429* (2013.01); *A61K 45/06* (2013.01)

(58) Field of Classification Search
USPC .......................................................... 514/366
See application file for complete search history.

(56) References Cited

U.S. PATENT DOCUMENTS

| 8,357,708 B2 * | 1/2013 | Luesch et al. ................. 514/366 |
| 2007/0185071 A1 * | 8/2007 | Yoshida et al. ............... 514/184 |
| 2011/0123644 A1 | 5/2011 | Luesch |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Boyce et al., Tetrahedron, 51:7313-7320 (1995).
Taori et al., J. Am. Chem. Soc., 130:1806-1807 (2008).
European Search Report dated Dec. 28, 2010, corresponding to EP Application No. 08829476.4.
Ying Y et al., "Total synthesis and molecular target of largazole, a histone deacetylase inhibitor", Journal of the American Chemical Society US, vol. 130, No. 26, Jul. 2, 2008, pp. 8455-8459.
Ren Q et al: "Total synthesis of largazole", SYNLETT Sep. 15, 2008 DE LNKD-DOI: 10.1055/S-2008-1078270, No. 15, Sep. 15, 2008, pp. 2379-2383, XP009142332, ISSN: 0936-5214.
Taori Kanchan et al., "Structure and Activity of Largazole, a potent antiproliferative agent from the Floridiqn marine cyanobacterium Symploca sp.", Journal of the American Chemical Society, vol. 130, No. 6, Feb. 2008, pp. 1806-1807, XP002614058, ISSN: 002-7863, p. 1806.
Nasveschuk et al., caplus an 2008:837585.
Extended European Search Report Dated Dec. 12, 2006 for EP Appln. No. 12181107.9
Japanese Office Action date Sep. 2, 2014 for JP Apppln. No. 2010-524059.
Japanese Office Action dated Jul. 9, 2013 for JP Appln. No. 2010-524059.
Ying, Y et al.; "Synthesis and Activity of Largazole Analogues With Linker and Macrocycle Modification"Organic Letters, Aug. 2008; vol. 10, No. 18; pp. 4021-4024.
Seiser T et al.; "Synthesis and Biological Activity of Largazole Derivatives"; Agnew Chem Int. Ed., Aug. 2008, vol. 47, pp. 6483-6485.

* cited by examiner

*Primary Examiner* — Kristin Vajda
(74) *Attorney, Agent, or Firm* — Locke Lord LLP; Jeffrey D. Hsi

(57) ABSTRACT

The instant invention describes macrocyclic compounds having therapeutic activity, and methods of treating disorders such as cancer, tumors and cell proliferation related disorders, or affect cell differentiation, dedifferentiation or transdifferentiation.

16 Claims, 9 Drawing Sheets

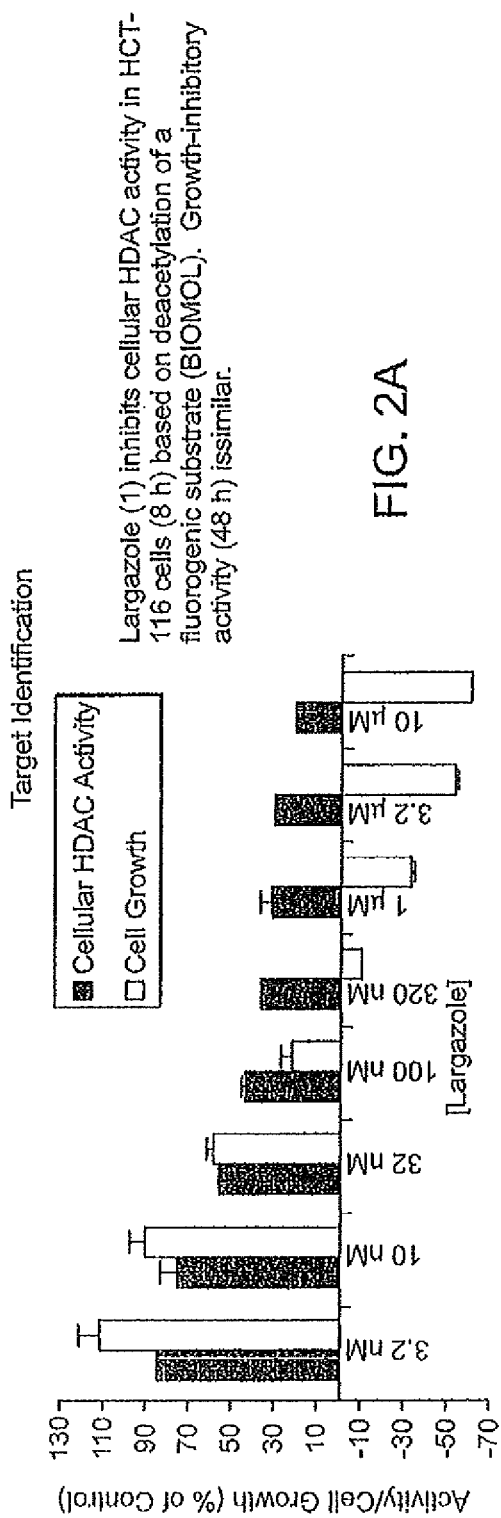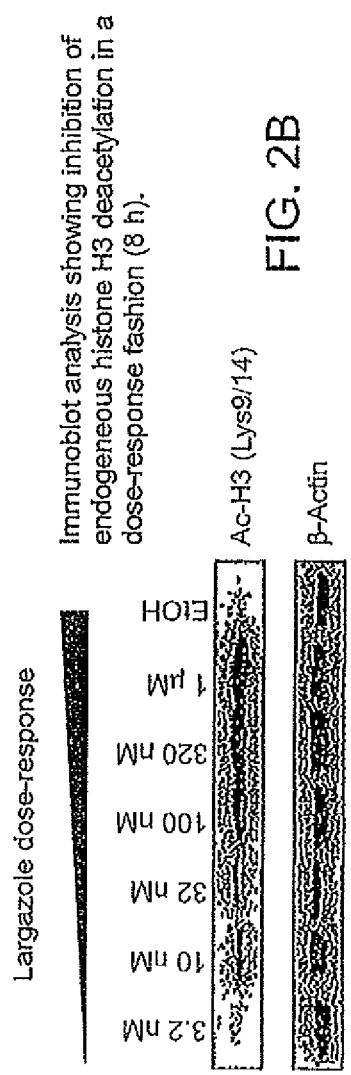
FIG. 2A
Largazole (1) inhibits cellular HDAC activity in HCT-116 cells (8 h) based on deacetylation of a fluorogenic substrate (BIOMOL). Growth-inhibitory activity (48 h) is similar.
FIG. 2B
Immunoblot analysis showing inhibition of endogeneous histone H3 deacetylation in a dose-response fashion (8 h).

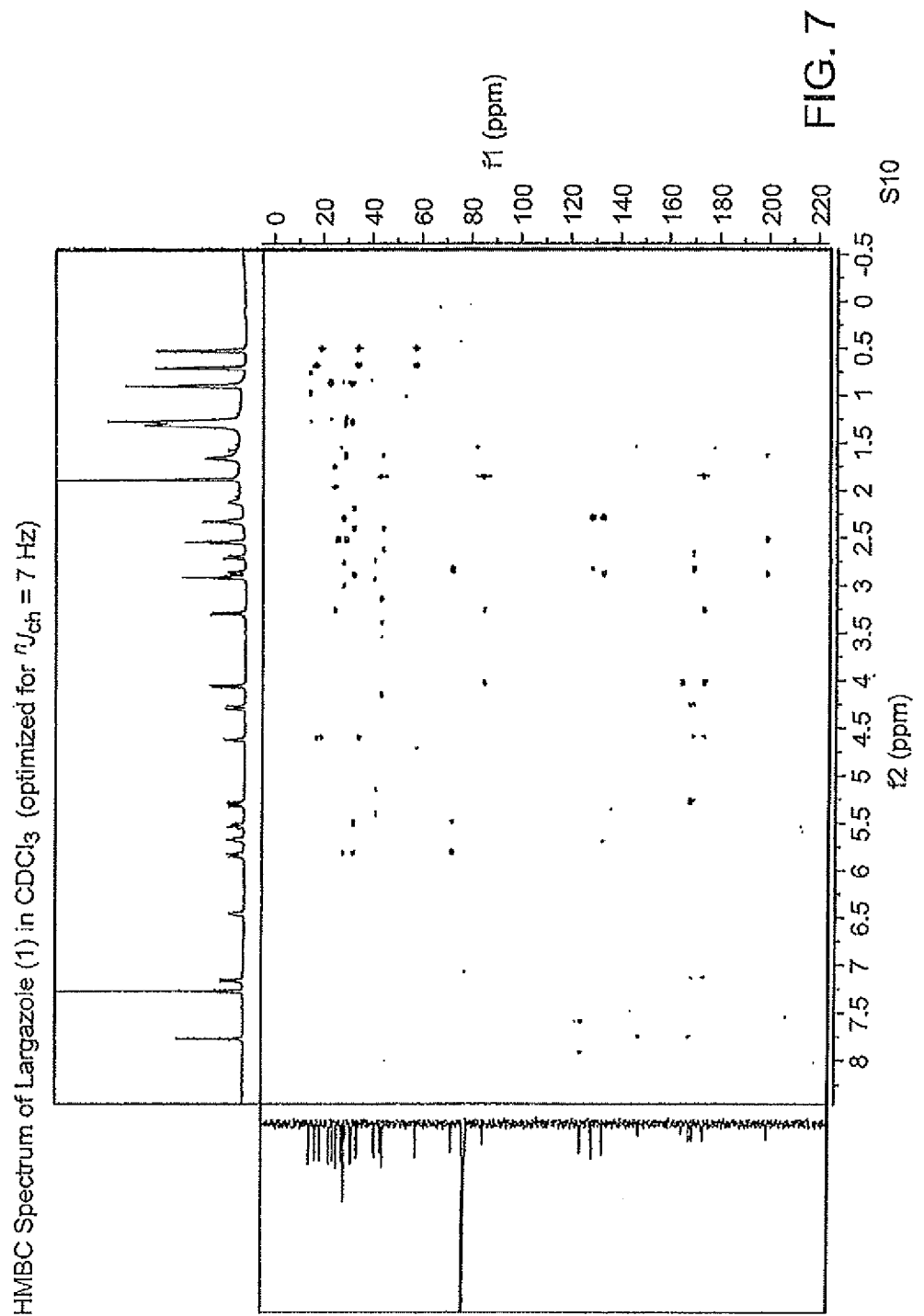

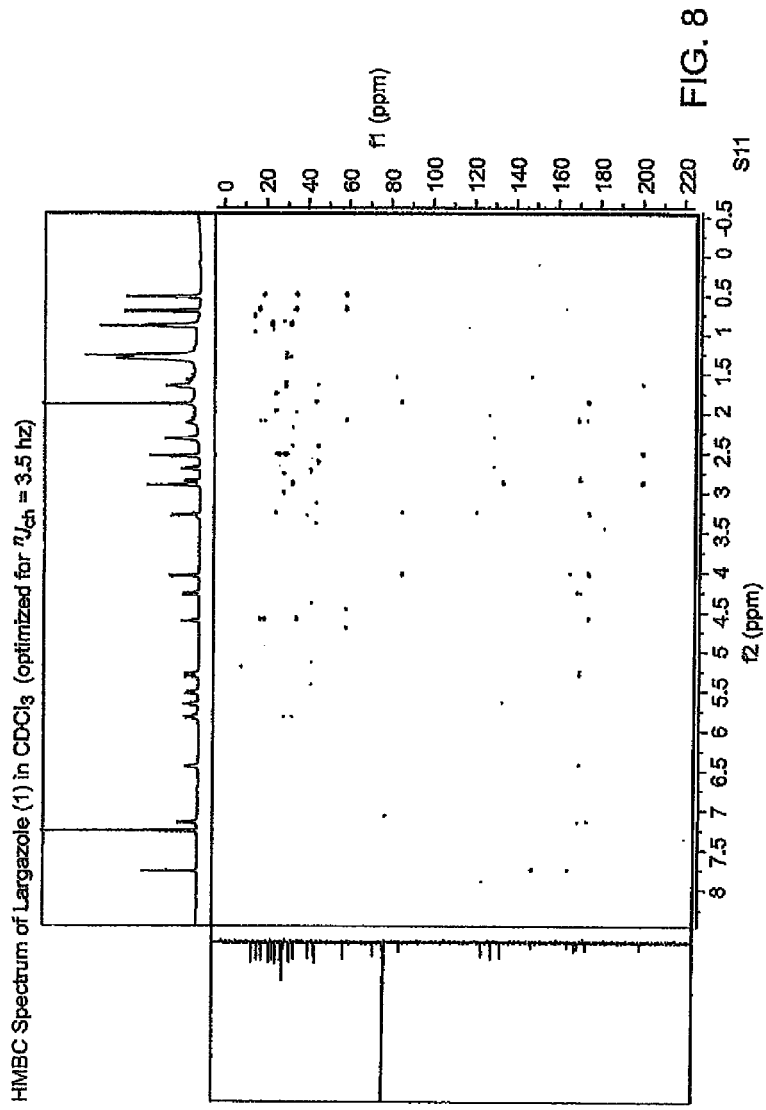

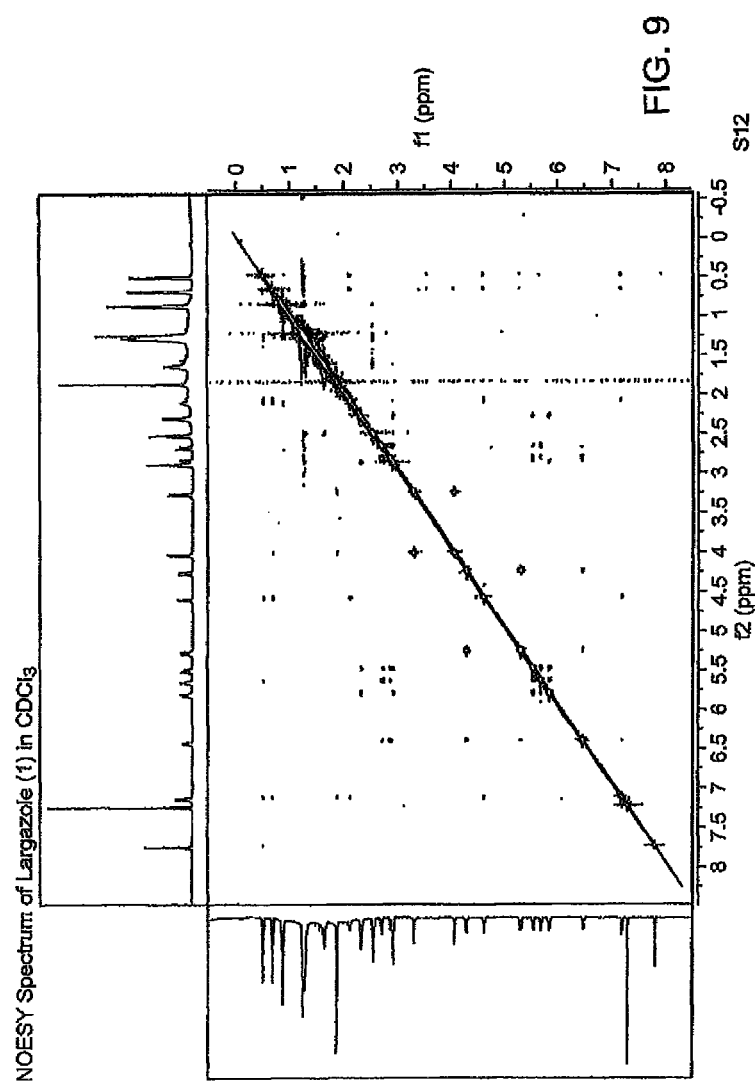

MACROCYCLIC COMPOUNDS AND METHODS OF TREATMENT

CROSS-REFERENCE TO RELATED APPLICATIONS

This application is a Continuation application of U.S. patent application Ser. No. 13/331,497, filed Dec. 20, 2011, which is a Divisional application of U.S. patent application Ser. No. 12/677,078, filed Dec. 2, 2010, which is a U.S. national stage entry of International Application No. PCT/US2008/010633, filed Sep. 9, 2008, which claims the benefit of U.S. Provisional Patent Applications Nos. 60/970,986, filed 9 Sep. 2007; 61/009,903, filed 3 Jan. 2008; 61/030,993, filed 24 Feb. 2008; 61/125,542, filed 24 Apr. 2008 and a Provisional Patent Application 61/189,093 filed 15 Aug. 2008, the entire teachings of which are hereby incorporated by reference.

This application claims the benefit of U.S. Provisional Patent Applications Nos. 60/970,986, filed 9 Sep. 2007; 61/009,903, filed 3 Jan. 2008; 61/030,993, filed 24 Feb. 2008; 61/125,542, filed 24 Apr. 2008 and a Provisional Patent Application 61/189,093 filed 15 Aug. 2008 which has not yet been assigned an application number, the entire teachings of which are hereby incorporated by reference.

STATEMENT OF RIGHTS TO INVENTIONS MADE UNDER FEDERALLY SPONSORED RESEARCH

This work was supported in part by a NOAA, Office of Sea Grant, U.S Department of Commerce Grant No. NA06OAR4170014. The government has certain rights in the invention.

BACKGROUND

The identification of new pharmacophores is of paramount biomedical importance and natural products have recently been regaining attention for this endeavor.[1] This renaissance is closely tied to the successful exploitation of the marine environment which harbors unmatched biodiversity that is presumably concomitant with chemical diversity.[2] In particular, marine cyanobacteria are prolific producers of bioactive secondary metabolites,[3] many of which are modified peptides or peptide-polyketide hybrids with promising antitumor activities, such as dolastatin 10,[4] curacin A,[5] and apratoxin A.[6] As a result of ongoing investigations to identify new drug leads from cyanobacteria in Florida, we report here the structure determination and preliminary biological characterization of a marine cyanobacterial metabolite with novel chemical scaffold and nanomolar antiproliferative activity. These findings provide new alternatives to address unmet needs in the treatment of proliferation diseases and disorders. The compounds herein are also now found to mediate histone deacetylase (HDAC) processes (e.g., inhibition) and as such are useful for treating diseases, disorders, or symptoms thereof mediated by inhibition of histone deacetylase (HDAC). These findings provide new alternatives to address unmet needs in the treatment of HDAC mediated diseases and disorders.

BRIEF SUMMARY OF THE INVENTION

The invention is directed towards macrocyclic compounds, and methods of treating disease and disorders, including proliferation diseases and disorders, and HDAC mediated diseases and disorders, by use of the compounds and compositions thereof.

The invention is directed towards macrocyclic compounds, methods of modulating proliferation activity, and methods of treating proliferation disease and disorders.

In one embodiment, the invention provides a compound according to Formula I:

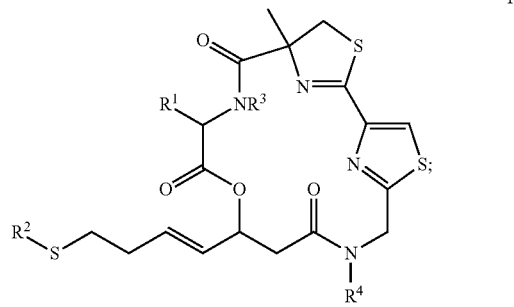

wherein:

each R is independently H or optionally substituted alkyl;

each $R^1$ is independently H, or optionally substituted alkyl;

each $R^2$ is independently H, optionally substituted alkyl, or C(O)R;

each $R^3$ is independently H, optionally substituted alkyl, C(O)OR, or C(O)NRR;

each $R^4$ is independently H, optionally substituted alkyl, C(O)OR, or C(O)NRR;

and pharmaceutically acceptable salts, solvates, or hydrates thereof.

Another aspect is a compound of formula Ia (and pharmaceutically acceptable salts, solvates, or hydrates thereof), where R, $R^1$, $R^2$, $R^3$, and $R^4$ are as defined in formula I:

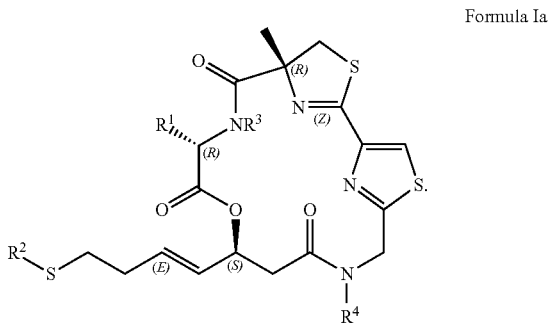

Formula Ia

Other embodiments include a compound of any of the formulae herein, wherein $R^3$ and $R^4$ are H; wherein $R^1$ is isopropyl; wherein $R^2$ is alkyl; wherein $R^2$ is alkylC(O)—; wherein $R^2$ is H; wherein the compound is any of Compounds 1-8 in Table A; or wherein the compound is largazole.

In certain instances, the compounds of the invention are selected from the following of Formula (I) (including formula Ia) having the structure:

TABLE A

| Cmpd No. | R¹ | R² | R³ | R⁴ |
|---|---|---|---|---|
| 1 | isopropyl | n-heptylC(O)— | H | H |
| 2 | isopropyl | n-heptylC(O)— | H | Me |
| 3 | isopropyl | Me | H | H |
| 4 | isopropyl | n-heptylC(O)— | H | methylC(O)— |
| 5 | isopentyl | n-heptylC(O)— | H | H |
| 6 | ethyl | n-heptylC(O)— | Me | Me |
| 7 | isopropyl | CH₃C(O)— | H | H |
| 8 | isopropyl | H | H | H |

In another aspect, the invention provides a pharmaceutical composition comprising the compound of formula I and a pharmaceutically acceptable carrier.

In other aspects, the invention provides a method of treating a disease, disorder, or symptom thereof in a subject, comprising administering to the subject a compound of any of the formulae herein (e.g., formula I, formula Ia). In another aspect, the compound is administered in an amount and under conditions sufficient to ameliorate the disease, disorder, or symptom thereof in a subject.

In other aspects, the invention provides a method of modulating HDAC activity in a subject, comprising contacting the subject with a compound of any of the formulae herein (e.g., formula I, formula Ia), in an amount and under conditions sufficient to modulate HDAC activity. In another aspect, the modulation is inhibition.

In other aspects, the invention provides a method of modulating the proliferation activity in a subject, comprising contacting the subject with a compound of formula I, in an amount and under conditions sufficient to modulate proliferation activity.

In one aspect, the invention provides a method of treating a subject suffering from or susceptible to a proliferation related disorder or disease, comprising administering to the subject an effective amount of a compound or pharmaceutical composition of formula I.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of formula I, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of formula I, such that cell proliferation in said subject is modulated (e.g., down regulated). In another aspect, the compounds delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., Formula I), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

In another aspect, the invention provides a method of inhibiting histone deacetylase (HDAC) in a subject in need thereof comprising administering to said subject, an effective amount of a compound delineated herein (e.g., Formula I), and pharmaceutically acceptable salts thereof.

In another aspect, the invention provides a method of treating diseases, disorders, or symptoms thereof mediated by inhibition of histone deacetylase (HDAC) in a subject in need thereof comprising administering to said subject, an effective amount of a compound delineated herein (e.g., Formula I), and pharmaceutically acceptable salts thereof. Recently, HDAC inhibitors have been found to ameliorate progression of the spinal muscular atrophy (SMA) motor neuron disease and the Huntington disease mouse models. The neuroprotective role of HDAC inhibitors seems to extend to other diseases that share mechanisms of oxidative stress, inflammation and neuronal cell apoptosis. HDAC inhibitors also have widespread modulatory effects on gene expression within the immune system and have been used successfully in the lupus and rheumatoid arthritis autoimmune disease models. Recently, the efficacy of the HDAC inhibitor Trichostatin A was established in ameliorating disease in the multiple sclerosis (MS) animal model, experimental autoimmune encephalomyelitis (EAE). In aspects, the compounds herein are useful to treat MS, an autoimmune, demyelinating and degenerative disease of the human central nervous system (CNS). In aspects the compounds herein are useful to treat stroke. In other aspects, the HDAC inhibitor compounds are useful to treat or prevent memory loss, for inducing neurogenesis, for enhancing memory retention, for enhancing memory formation, for increasing synaptic potential or transmission, or for increasing long term potentiation (LTP). Histone deacetylases (HDAC) are also associated with a variety of transcriptional repressors that control cellular differentiation and proliferation. Modulation of gene expression through HDAC inhibition may control stem cell fate and affect differentiation, dedifferentiation or transdifferentiation. Thus, the compounds herein are useful to improve reprogramming efficiency; enable efficient induction of pluripotent stem cells; cause pluripotent stem cells to cease proliferating and enter terminal differentiation pathways; to inhibit differentiation to oligodendrocytes, where HDAC2 activity specifically inhibits differentiation to astrocytes, while HDAC1 activity is required for differentiation to neurons; enhance differentiation in stem cell therapy, be used as medium supplements that stabilize the phenotype of primary cells in culture; stimulate osteoblast maturation; implement-bone tissue engineering; induce myogenic differentiation; up-regulat basal activity of transcription from a MyoD-responsive reporter; and induce ex vivo expansion of human hematopoietic stem cells (HSC). In aspects the compounds herein are useful to treat conditions in a subject including but not limited to myogenesis, neurogenesis, osteogenesis and osteoblast maturation.

In another aspect, the invention provides a method of treating diseases, disorders, or symptoms in a subject in need thereof comprising administering to said subject, an effective amount of a compound delineated herein (e.g., Formula I), and pharmaceutically acceptable salts thereof. Such methods are useful for treating memory loss, inducing neurogenesis, enhancing memory retention, enhancing memory formation, increasing synaptic potential or transmission, or increasing long term potentiation (LTP). Such methods are also useful for treating diseases and disorders associated with stem cell fate and that are affected by differentiation, dedifferentiation or transdifferentiation, and thus include but not limited to myogenesis, neurogenesis, osteogenesis and osteoblast maturation.

In another aspect, the compounds of any of the formulae herein (e.g., formula (I)) are compounds having class I HDAC selectivity, thus they are useful as anticancer agents; and furthermore having selectivity for class I HDAC versus class II HDAC also provides a more desirable therapeutic profile as it is indicated that inhibition of certain specific class II HDACs may have undesirable consequences, including for example, promoting cardiac hypertrophy. See, Furumai et al. Cancer Research 2002, 62, 4916-4921; Yurek-George et al. J. Med. Chem. 2007, 50, 5720-5726. Thus, in one aspect, the compounds and methods herein are those wherein the compounds demonstrate selectivity in class I/class II HDAC selectivity (e.g., at least 2-fold, at least 10-fold, at least 100-fold, at least 1000-fold, at least X-fold where X is any number between 1 and 100,000 inclusive).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which:

FIG. 2. depicts A) HDAC inhibition and growth-inhibitory results with largazole in HCT-116 cells; and B) immunoblot analysis with largazole demonstrating H3 deacetylation.

FIG. 1 depicts the $^1$H NMR spectrum of largazole in CDCl$_3$.

FIG. 7. depicts the HMBC spectrum of largazole in CDCl$_3$ (optimized for $^nJ_{ch}$=3.5 hz).

FIG. 8. depicts the HMBC spectrum of largazole in CDCl$_3$ (optimized for $^nJ_{ch}$=7 hz).

FIG. 9. depicts the NOESY spectrum of largazole in CDCl$_3$.

DETAILED DESCRIPTION

Definitions

Figure 1:
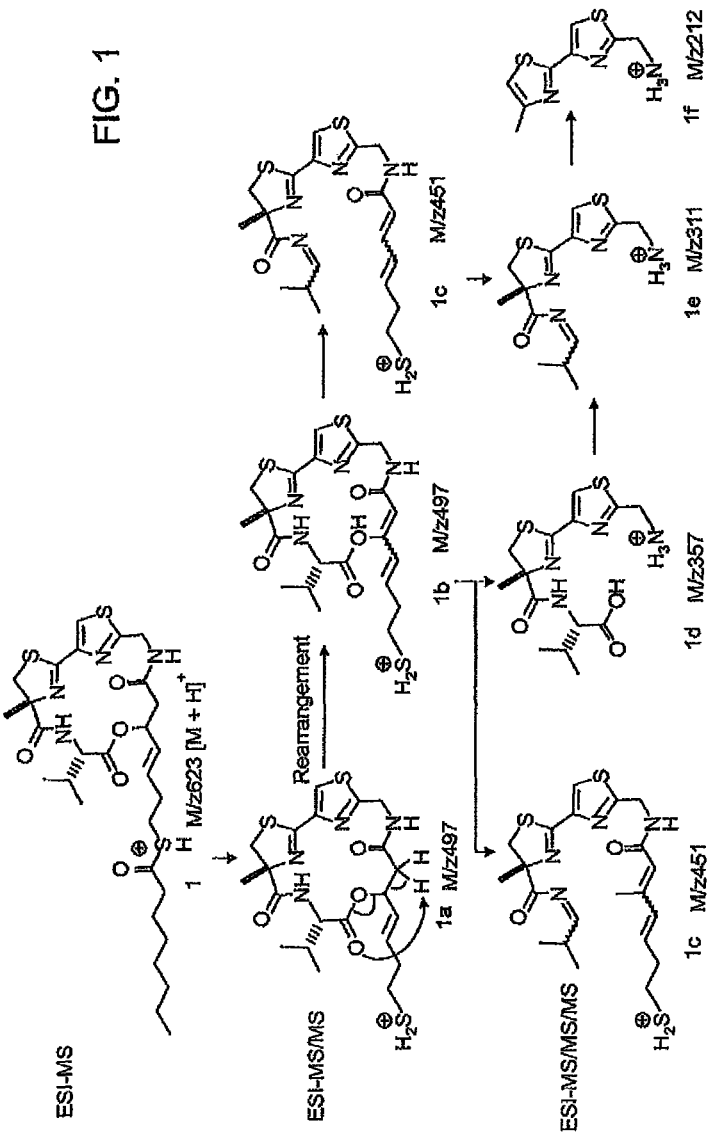
FIG. 1. depicts largazole dissociation pathways and structures of product ions.
Figure 3:
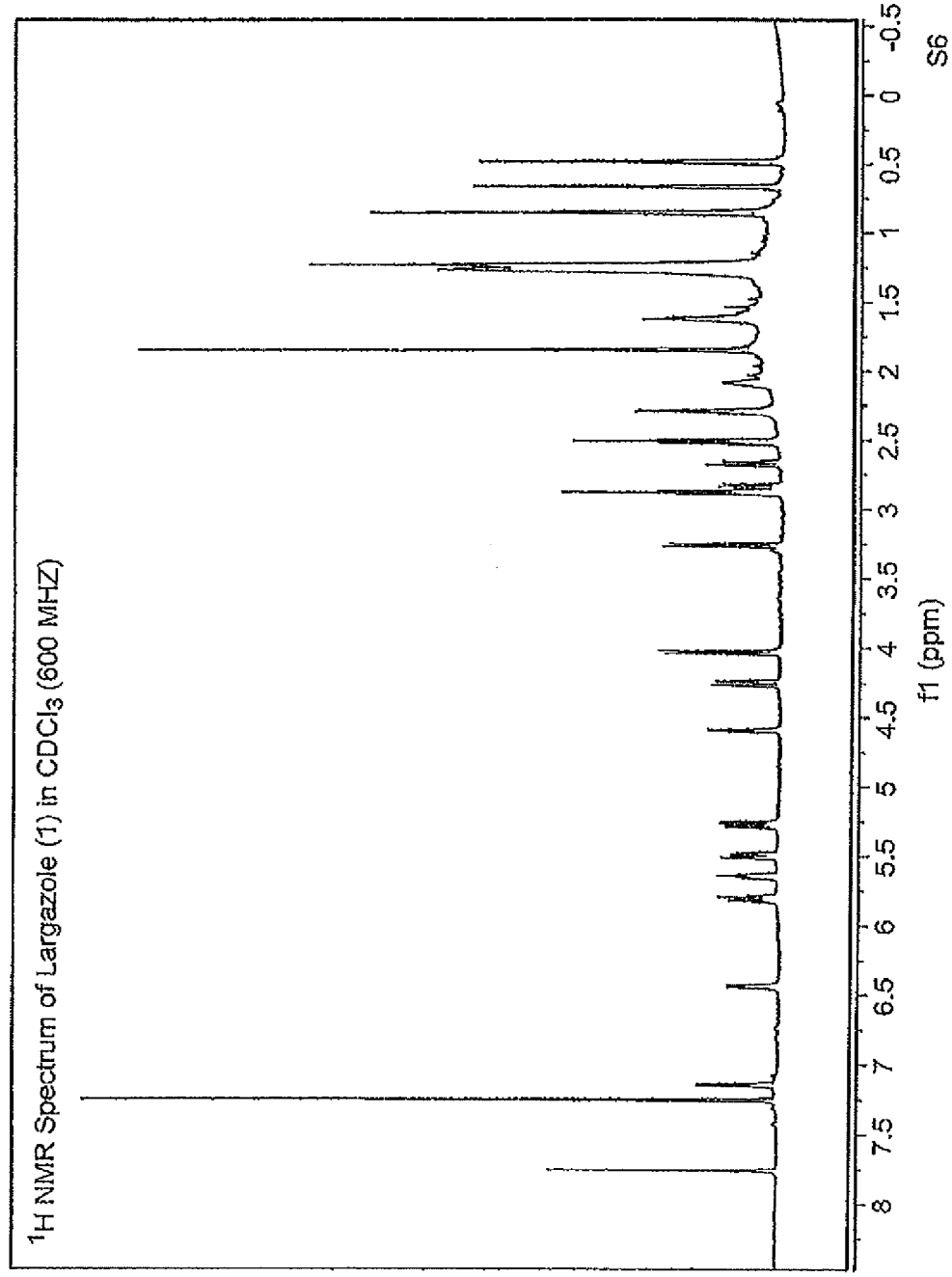
Figure 4:
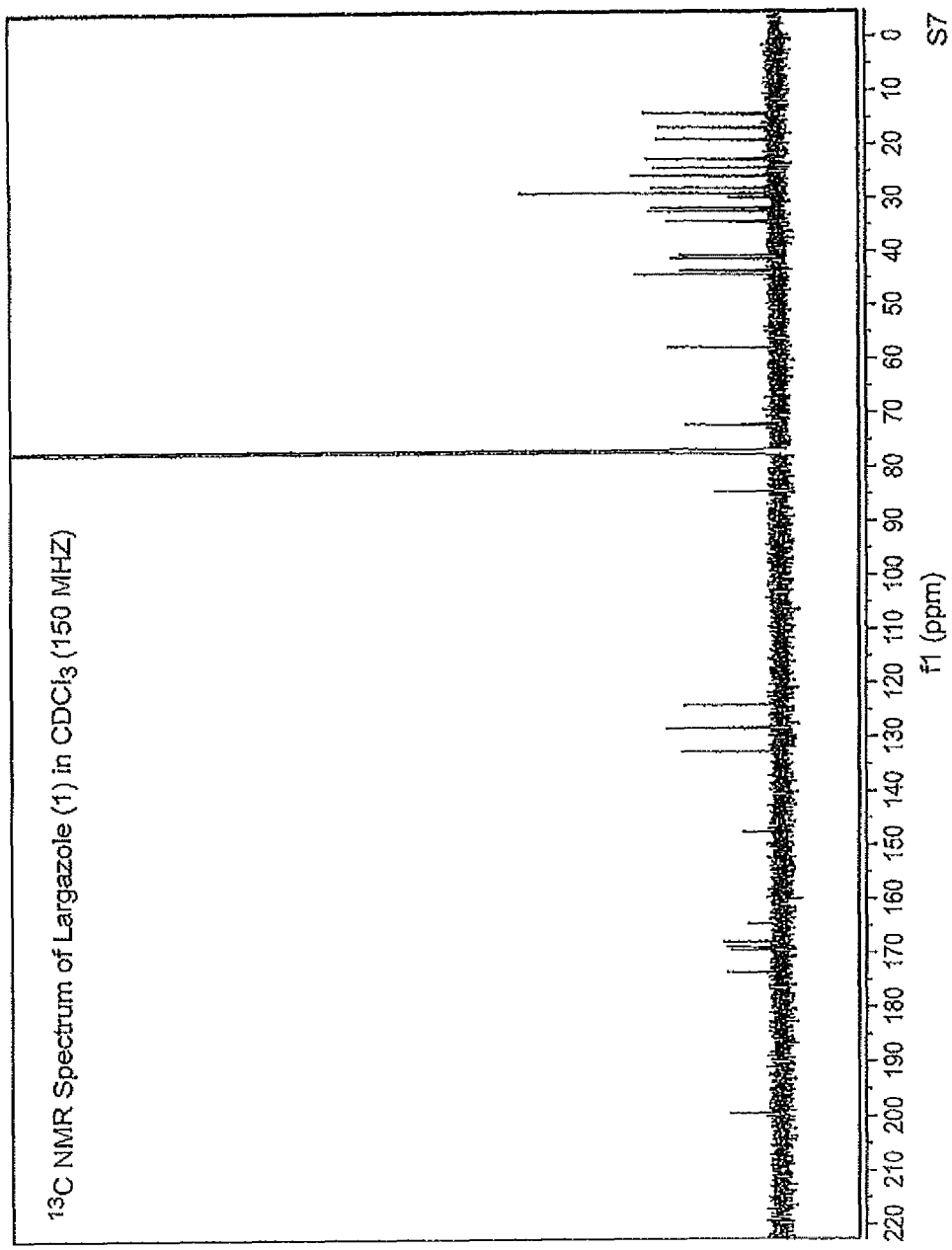
FIG. 4. depicts the $^{13}$C NMR spectrum of largazole in CDCl$_3$.
Figure 5:
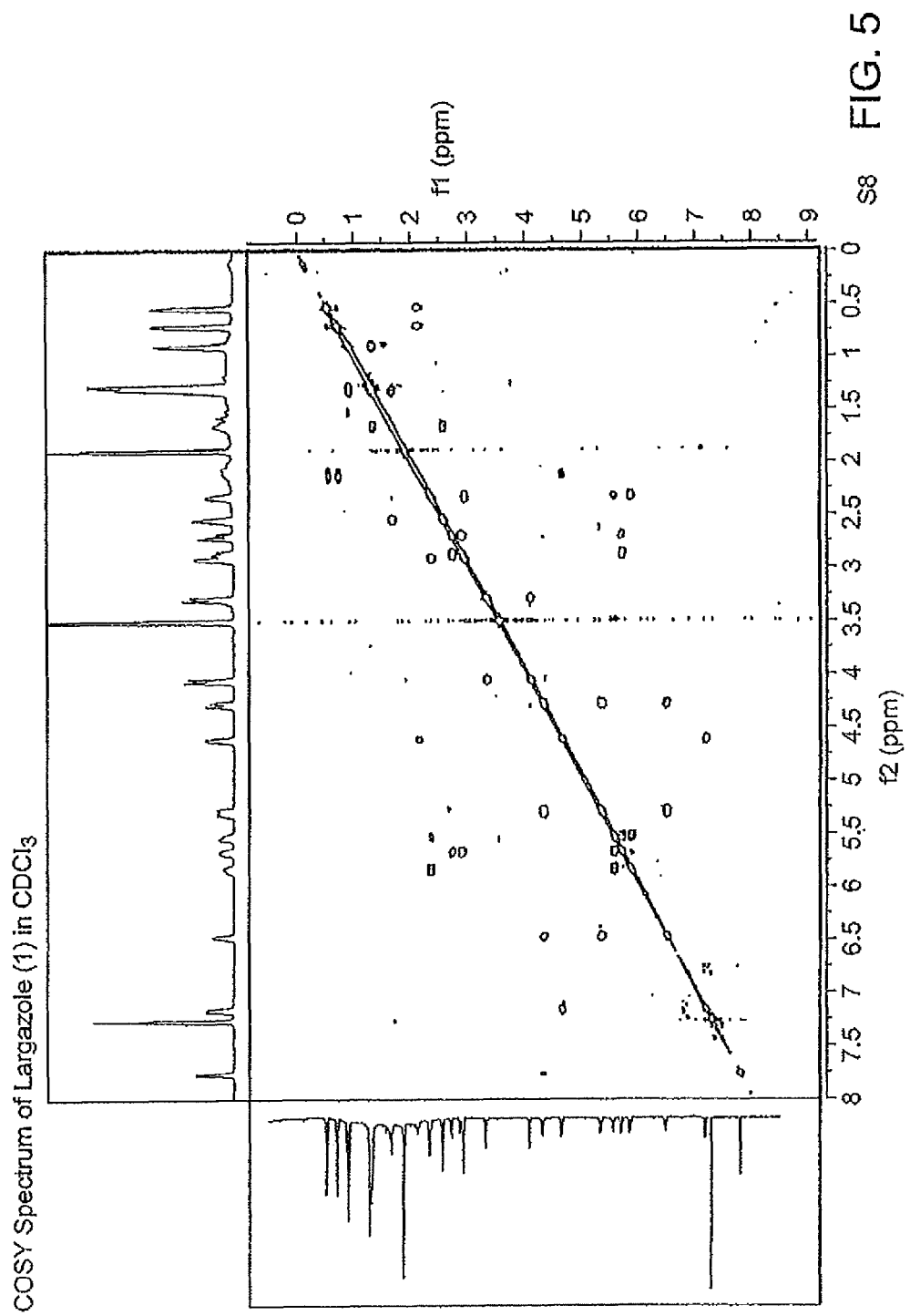
FIG. 5. depicts the COSY spectrum of largazole in CDCl$_3$.
Figure 6:
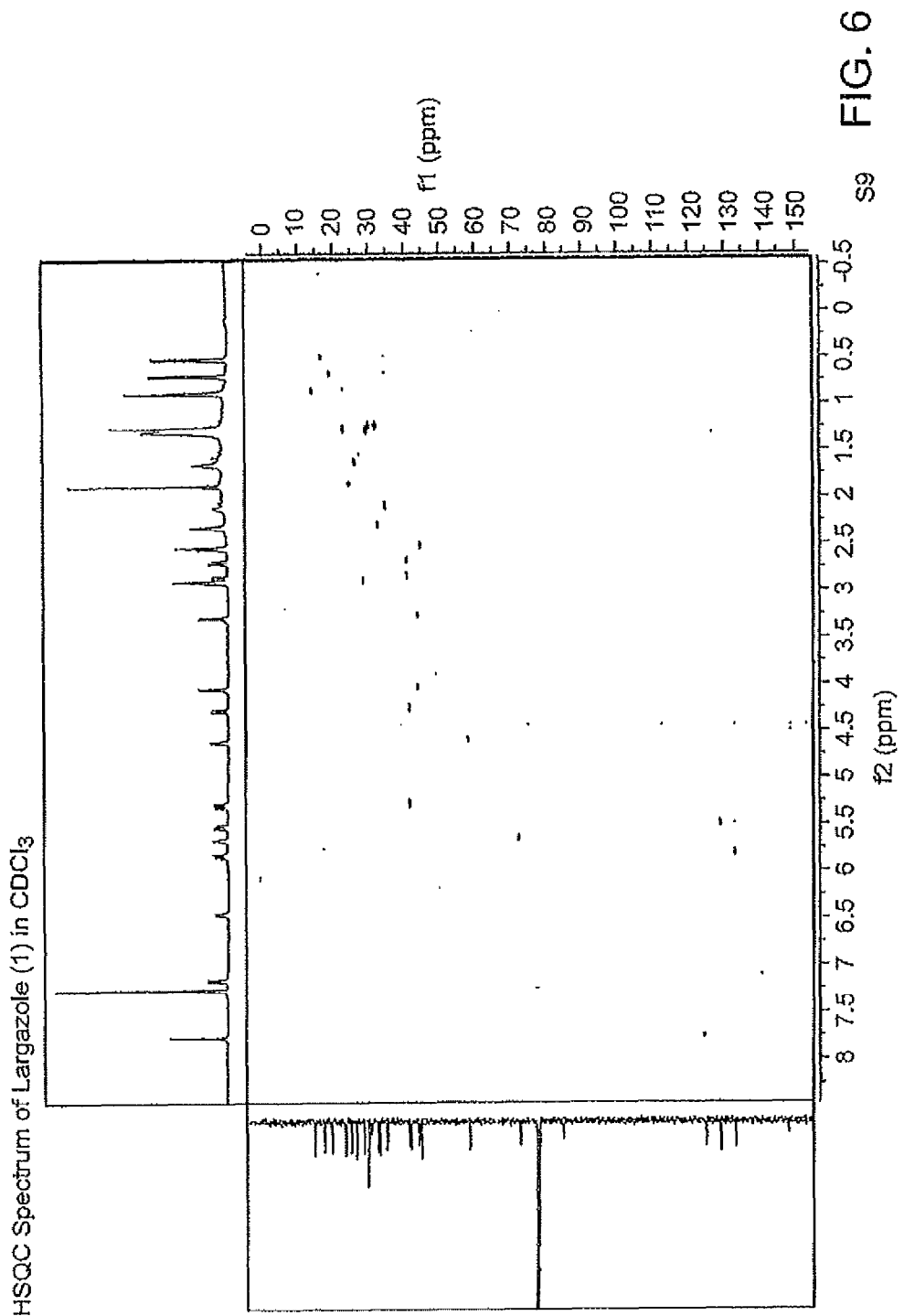
FIG. 6. depicts the HSQC spectrum of largazole in CDCl$_3$.

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, acyloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or acylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention and Structure Elucidation

A sample of *Symploca* sp. was collected from Key Largo, Florida Keys and extracted with organic solvents. The resulting cytotoxic crude extract was subjected to bioassay-guided fractionation by solvent partition, silica gel chromatography and reversed-phase HPLC to yield largazole (1) as a colorless, amorphous solid $\{[\alpha]^{20}{}_D+22$ (c 0.1, MeOH)$\}$.

Largazole (1)

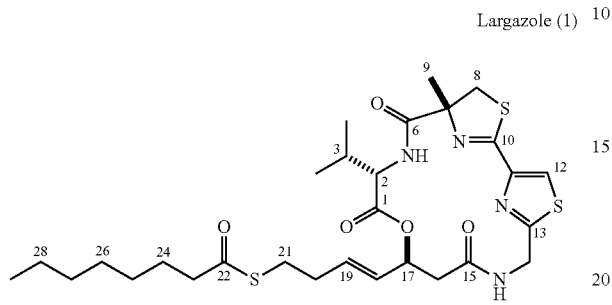

$^1$H and $^{13}$C NMR data coupled with a [M+H]$^+$ peak at m/z 623.2397 in the HR-ESI/APCI-MS of 1 suggested a molecular formula of $C_{29}H_{42}N_4O_5S_3$ (calcd for $C_{29}H_{43}N_4O_5S_3$, 623.2396). The $^1$H NMR spectrum exhibited two signals characteristic for secondary amides ($\delta_{2\text{-}NH}$ 7.15, $\delta_{14\text{-}NH}$ 6.45). Further two-dimensional NMR analysis in CDCl$_3$ using COSY, HSQC and HMBC data indicated that these exchangeable protons belong to valine and modified glycine residues, respectively (Table 1 and Supporting Information). The putative glycine carbonyl ($\delta_{C\text{-}13}$ 167.9) was part of a 2,4-disubstituted thiazole unit as evidenced by HMBCs from the only aromatic methine ($\delta_{H\text{-}12}$ 7.76, $\delta_{C\text{-}12}$ 124.2) to C-13 and to another quaternary sp$^2$ carbon, C-11 ($\delta_C$ 147.4). Furthermore, HMBCs from a methyl singlet ($\delta_{H\text{-}9}$ 1.87) to carbonyl C-6 ($\delta_C$ 173.5), quaternary carbon C-7 ($\delta_C$ 84.4) and methylene carbon C-8 ($\delta_C$ 43.3), combined with an HMBC from H-8a ($\delta_H$ 4.04) to C-10 ($\delta_C$ 164.6) suggested the presence of a 2-substituted thiazoline-4-methyl-4-carboxylic acid unit (C-6 to C-10). The only other HMBC to C-10 was from the thiazole proton H-12, indicating that C-10 bore the thiazole substituent. The methyl thiazoline carboxylate and the amino terminus of the valine residue were unambiguously connected via an amide linkage based on HMBC data (Table 1). The remaining signals in the $^1$H NMR spectrum belonged to two spin systems, as concluded from COSY analysis (Supporting information). One of the units was a 7-substituted 3-hydroxy-hept-4-enoic acid moiety (C-15 to C-21) with E-geometry of the double bond based on a large coupling constant for $^3J_{H\text{-}18,H\text{-}19}$ of 15.6 Hz, consistent with NOESY cross peaks between H-18 and H$_2$-20. This unit was attached to the amino terminus of the glycine-derived unit as shown by HMBCs from 14-NH and H-14a/b to C-15 as well as ROESY cross peaks between 14-NH and H-16a and H-16b. The last unit was an n-octanoyl group (C-22 to C-29) which was connected with C-21 based on HMBC from H$_2$-21 to C-22. The low-field chemical shift for C-22 ($\delta_C$ 199.4) coupled with the fact that one sulfur atom yet remained to be assigned was strong evidence for a thioester functionality. Finally, to account for the molecular formula requirements and for the low-field chemical shift of H-17 ($\delta_H$ 5.66) suggestive of an acyloxy substituent, C-17 had to be ester-linked to the carboxyl terminus of valine. This was further supported by a weak NOE between H-17 and H$_3$-5 ($\delta_H$ 0.50), leading to the cyclic planar structure shown for 1.

To assign the absolute configuration of the three chiral centers, our strategy was to generate optically active fragments, for which enantiomeric standards are readily available (Scheme 1). Specifically, ozonolysis followed by oxidative work-up and acid hydrolysis generated 2-methylcysteic acid, valine and malic acid. The product mixture was subjected to chiral HPLC analysis, comparing retention times with those of authentic standards. This analysis identified L-valine, (R)-2-methylcysteic acid and i-malic acid, establishing the absolute configuration of 1 as 2S,7R,17S.

TABLE 1

NMR Spectral Data for Largazole (1) in CDCl$_3$ (600 MHz)

| C/H no. | $\delta_H$ (J in Hz) | $\delta_c$, mult. | HMBC$^{ab}$ |
|---|---|---|---|
| 1 | | 168.9, qC | |
| 2 | 4.61, dd (9.2, 3.3) | 57.7, CH | 1, 3, 4, 5, 6 |
| 3 | 2.10, m | 34.2, CH | 1,$^c$ 2$^c$ |
| 4 | 0.68, d (7.2) | 18.9, CH$_3$ | 2, 3, 5 |
| 5 | 0.50, d (7.2) | 16.6, CH$_3$ | 2, 3, 4 |
| 2-NH | 7.15, d (9.2) | | 1, 6$^c$ |
| 6 | | 173.5, qC | |
| 7 | | 84.4, qC | |
| 8a | 4.04, d (−11.4) | 43.3, CH$_2$ | 6, 7, 10 |
| 8b | 3.27, d (−11.4) | | 6, 7, 9 |
| 9 | 1.87, br s | 24.2, CH$_3$ | 6, 7, 8 |
| 10 | | 164.6, qC | |
| 11 | | 147.4, qC | |
| 12 | 7.76, s | 124.2, CH | 10,$^c$ 11, 13 |
| 13 | | 167.9, qC | |
| 14a | 5.29, dd (−17.4, 9.6) | 41.1, CH | 13, 15 |
| 14b | 4.27, dd (−17.4, 2.5) | | 13, 15 |
| 14-NH | 6.45, dd (9.6, 2.5) | | 15$^c$ |
| 15 | | 169.4, qC | |
| 16a | 2.86, dd (−16.5, 10.5) | 40.5, CH$_2$ | 15, 17, 18 |
| 16b | 2.68, dd (−16.5, 1.8) | | 15 |
| 17 | 5.66, ddd (10.5, 7.2, 1.8) | 72.0, CH | |
| 18 | 5.51, dd (15.6, 7.2) | 128.4, CH | 17, 20 |
| 19 | 5.82, dt (15.6, 7.2) | 132.7, CH | 17, 20 |
| 20 | 2.31, br q (7.2) (2H) | 32.3, CH$_2$ | 18, 19, 21 |
| 21 | 2.90, t (7.2)(2H) | 27.9, CH$_2$ | 19, 20, 22 |
| 22 | | 199.4, qC | |
| 23 | 2.52, t (7.5) (2H) | 44.1, CH$_2$ | 22, 24, 25 |
| 24 | 1.64, m (2H) | 25.6, CH$_2$ | 22, 23, 25/26 |
| 25 | 1.29, m (2H) | 28.9, CH$_2$ | 26 |
| 26 | 1.25, m (2H) | 28.9, CH$_2$ | 25, 27 |
| 27 | 1.26, m (2H) | 31.6, CH$_2$ | |
| 28 | 1.28, m (2H) | 22.6, CH$_2$ | |
| 29 | 0.87, br t (6.9) | 14.0, CH$_3$ | 27, 28 |

$^a$Protons showing HMBC correlations to the indicated carbon.
$^b$Optimized for "J = 7 Hz if not indicated otherwise.
$^c$Optimized for " J = 3.5 Hz.

Scheme 1: Degradation strategy to liberate chiral subunits

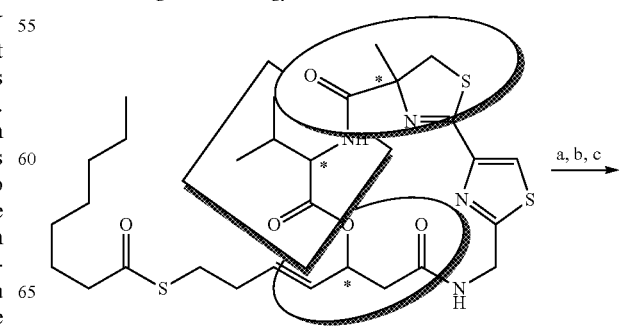

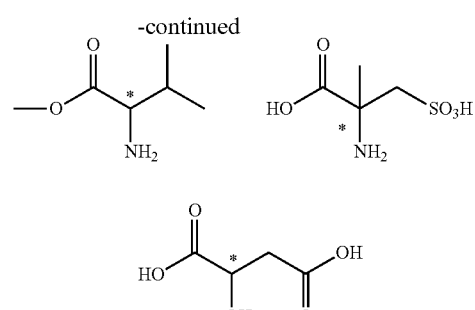

a) O₃, CH₂Cl₂, 25° C., 30 min;
b) H₂O₂—HCO₂H (1:2), 70° C., 20 min; c) 6N HCl, 110° C., 24h Largazole (1) possesses a dense combination of unusual structural features, including a substituted 4-methylthiazoline linearly fused to a thiazole, previously only found in didehydromirabazole,[7] a member of the group of terrestrial cyanobacteria) cytotoxins from *Scytonema mirabile* with solid tumor selectivity.[8] Another remarkable structural element is the thioester moiety; thioester-containing secondary metabolites have been reported previously from sponges,[9] eukaryotic algae[10] and bacteria,[11] but not from cyanobacteria. The 3-hydroxy-7-thio-hept-4-enoic acid unit in 1 is unprecedented in natural products. Most significantly, the potent biological activity and selectivity for cancer cells warrants further investigation as to the mode of action, cancer chemotherapeutic potential and biosynthesis of largazole (1).

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$* Edition, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet, search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regio isomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

The invention is directed towards macrocyclic compounds, and methods of treating disease and disorders using the compounds or compositions thereof delineated herein.

In other aspects, the invention provides a method of treating a subject suffering from or susceptible to HDAC related disorder or disease, wherein the subject has been identified as in need of treatment for a HDAC related disorder or disease, comprising administering to said subject in need thereof, an effective amount of a compound or pharmaceutical composition of formula I, such that said subject is treated for said disorder. Identifying a subject in need of such treatment can be in the judgment of a subject or a health care professional and can be subjective (e.g. opinion) or objective (e.g. measurable by a test or diagnostic method).

In one aspect, the invention provides a method of modulating the proliferation activity of a cell in a subject, comprising contacting the subject with a compound of formula I, in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of formula I.

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof; an effective amount of a compound or pharmaceutical composition of formula I, such that said subject is treated for said disorder.

In certain embodiments, the invention provides a method as described above, wherein the compound of formula I is largazole.

In certain embodiments, the invention provides a method of treating a disorder, wherein the disorder is cancer (e.g., breast, colon) or solid tumor.

In certain embodiments, the subject is a mammal, preferably a primate or human.

In another embodiment, the invention provides a method as described above, wherein the effective amount of the compound of formula I ranges from about 0.005 µg/kg to about 200 mg/kg. In certain embodiments, the effective amount of the compound of formula I ranges from about 0.1 mg/kg to about 200 mg/kg. In a further embodiment, the effective amount of compound of formula I ranges from about 10 mg/kg to 100 mg/kg.

In other embodiments, the invention provides a method as described above wherein the effective amount of the compound of formula I ranges from about 1.0 pM to about 500 nM. In certain embodiments, the effective amount ranges from about 10.0 pM to about 1000 pM. In another embodiment, the effective amount ranges from about 1.0 nM to about 10 nM.

In another embodiment, the invention provides a method as described above, wherein the compound of formula I is administered intravenously, intramuscularly, subcutaneously, intracerebroventricularly, orally or topically.

In another embodiment, the invention provides a method as described herein wherein the compound of formula I demonstrates selectivity (e.g., at least 2-fold, at least 5-fold, at least 10-fold, at least X-fold where X is any number between 1 and 20 inclusive) in cell growth activity (e.g., in transformed/nontransformed, MDA-MB-231/NMuMG, U2OS/NIH3T3 cells). In another aspect, the compound of formula I demonstrates selectivity in modulating cell growth activity (e.g., at least 2-fold, at least 5-fold, at least 10-fold, at least X-fold where X is any number between 1 and 20 inclusive) relative to another standard anticancer therapy (e.g., paclitaxel, actinomycin D, doxorubicin).

In other embodiments, the invention provides a method as described above, wherein the compound of formula I is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease, or to affect cell differentiation, dedifferentiation or transdifferentiation. Another object of the present invention is the use of a compound as described herein (e.g., of any formulae herein) for use in the treatment of a cell proliferation disorder or disease, or affect cell differentiation, dedifferentiation or transdifferentiation.

Pharmaceutical Compositions

In one aspect, the invention provides a pharmaceutical composition comprising the compound of formula I and a pharmaceutically acceptable carrier.

In one embodiment, the invention provides a pharmaceutical composition wherein the compound of formula I is largazole, and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of formula I, in unit dosage form, together with instructions for administering the compound to a subject suffering from or susceptible to a HDAC mediated disease or disorder, including memory loss, inducing neurogenesis, enhancing memory retention, enhancing memory formation, increasing synaptic potential or transmission, or increasing long term potentiation (LTP), etc.

In one aspect, the invention provides a kit comprising an effective amount of a compound of formula I, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The present invention will now be demonstrated using specific examples that are not to be construed as limiting.

General Experimental Procedures $^1$H and $^{13}$C NMR data were acquired on a Bruker Avance 600 MHz spectrometer with a 5-mm probe operating at 600 and 150 MHz, respectively. 2D NMR data were recorded on a Bruker Avance II 600 MHz equipped with a 1-mm triple resonance high-temperature superconducting cryogenic probe using residual solvent signals ($\delta_H$7.26 ppm, $\delta_C$ 77.0 ppm) as internal standards. The HSQC experiments were optimized for $^1J_{CH}$=145 Hz, and the HMBC experiments for $^nJ_{CH}$=7 or 3.5 Hz. LC-MS data were obtained using an Agilent 1100 equipped with a ThermoFinnigan LCQ by ESI (positive mode). FIRMS data were obtained using an Agilent LC-TOF mass spectrometer equipped with an ESI/APCI multimode ion source detector. Enantiomeric standards of 2-methylcysteic acid were obtained by oxidation of (R)— and (S)-2-methylcysteines (see below) which were provided by ResCom (DSM Pharma Chemicals). Valine, glycine and malic acid standards were obtained from Sigma. Paclitaxel, actinomycin D and doxorubicin were obtained from EMD Chemicals, Inc.

Example 1

Extraction and Isolation

A sample of *Symploca* sp, was collected from Pillars, Key Largo (Florida Keys, USA) in August 2003. The specimens had upright, golden-brown, feather-like filaments consistent with this genus. Filaments measured 5-6 μm in width including a fine sheath and 8-9 μm in length. *Symploca* sp. was freeze-dried and extracted with MeOH-EtOAc (1:1). The resulting lipophilic extract (0.29 g) was partitioned between hexanes and 20% aqueous MeOH. The aqueous MeOH layer was concentrated and fractionated by Si gel chromatography using $CH_2Cl_2$ containing increasing amounts of i-PrOH followed by MeOH. The fraction that eluted with 5% i-PrOH was then subjected to reversed-phase HPLC (YMC-pack ODS-AQ, 250×10 mm, 2.0 mL/min; detection at 220 and 254 nm) using a MeOH—$H_2O$ linear gradient (40-100% for 75 min and then 100% MeOH for 10 min). Compound I eluted at $t_R$ 61.5 min (1.2 mg).

Largazole (1): colorless, amorphous solid; $[\alpha]^{20}_D$ +22 (c 0.1, MeOH); UV (MeOH) (log ε) 210 (4.07), 260 (sh) (3.61); IR (film) $v_{max}$ 2924, 2853, 1725, 1694, 1611, 1659, 1641, 1630, 1596, 1512, 1249, 1117, 1067, 1034, 894 cm$^{-1}$; $^1$H NMR, $^{13}$C NMR, and HMBC data, see Table 1; HR-ESI/APCI-MS m/z [M+H]$^+$623.2397 (calcd for $C_{29}H_{43}N_4O_5S_3$ 623.2396).

LC-MS$^n$ Analysis. A sample of compound 1 was analyzed by LC-MS [column: Waters Corp., Atlantis dC18 3 μm, 2.1×150 mm; mobile phase: 0.5% HCOOH in MeOH (A) in 0.5% HCOOH in $H_2O$ (B); flow rate: 0.15 mL/min] using a linear gradient (5-95% for 65 min). (+) ESI-MS (m/z 200-1600) of the most intense ion of the MS range ($t_R$ 51.1 min, m/z 623) as well as MS/MS and dependent MS/MS/MS of the m/z 623 [M+H]$^+$ ion was carried out (See, FIG. 1).

Example 2

Synthesis of (R)- and (S)-2-methylcysteic acid

A sample of (R)-2-methylcysteine (5.0 mg) was treated with 2 mL of a mixture of H2O2-HCO$_2$H (1:9) at 0° C. for 2 h. The product mixture was concentrated to dryness by evaporation to give (R)-2-methylcysteic acid. The residue was then reconstituted in 250 μL of $H_2O$ for amino acid analysis by chiral HPLC. Similarly, (S)-2-methylcysteine was reacted to yield (S)-2-methylcysteic acid.

Example 3

Determination of Absolute Configuration

A sample of compound 1 (~100 mg) was dissolved in 4 mL of $CH_2Cl_2$ and subjected to ozonolysis at room temperature for 30 min. The solvent was evaporated and the residue was treated with 0.6 mL of $H_2O_2$—$HCO_2H$ (1:2) at 70° C. for 20 min. The solvent was evaporated and the resulting oxidation product was hydrolyzed with 0.5 mL of 6 N HCl at 110° C. for 24 h. The hydrolyzed product was dried and analyzed by chiral HPLC (column, Phenomenex Chirex phase 3126 N,S-dioctyl-(D)-pencillamine, 4.60×250 mm, 5 μm; solvent 1, 2 mM $CuSO_4$ in 95:5 $H_2O$/MeCN, pH 4.50; solvent 2, 0.5 mM Cu(OAc)$_2$/0.1 M $NH_4OAc$ in 85:15 $H_2O$/MeCN, pH 4.6; flow rate 1.0 mL/min; detection at 254 nm). The absolute configuration of the amino acids in the hydrolyzate was determined by direct comparison with the retention times of authentic standards. The retention times ($t_R$, min) for solvent 1 were as follows: Gly (5.3), L-Val (12.6), D-Val (16.4), (S)-2-Me-cysteic acid (20.0), and (R)-2-Me-cysteic acid (23.9). The retention times ($t_R$, min) of the hydrolyzate components were 5.3, 12.6, 23.9, indicating the presence of Gly, L-Val and (R)-2-Me-cysteic acid in the product mixture. Solvent 2 was used to detect malic acid. Standard L-malic acid eluted at $t_R$, 7.6 min and D-malic acid at $t_R$ 20.4 min. Malic acid in the hydrolyzate eluted after 7.6 min, indicating the presence of the L isomer. Gly, L-Val, and (R)-2-Me-cysteic acid doted after 4.0, 5.8 and 6.5 min, respectively.

Example 4

Cell Culture

Cell culture medium was purchased from Invitrogen and fetal bovine serum (FBS) from Hyclone. Cells were propagated and maintained in DMEM medium (high glucose) supplemented with 10% FBS at 37° C. humidified air and 5% $CO_2$.

Example 5

Cell Viability Assays

Cells suspended in DMEM containing 10% FBS were plated in 96-well plates (MDA-MB-231: 12,000 cells; NMuMG: 5,000 cells; U20S: 5,000 cells; HT29: 10,000 cells; 1MR-32: 30,000 cells; NIH3T3: 5,000 cells) incubated (37° C., 5% $CO_2$) and 24 h later treated with various concentrations of compound 1 or solvent control (1% EtOH). After another 48 h of incubation, cell viability was measured using MITT according to manufacturer's instructions (Promega).

Example 6

Anticancer Therapeutics Activity

MDA-MB-231 and NMuMG cells were also treated with paclitaxel (in DMSO), actinomycin D (in DMSO) and doxorubicin (in $H_2O$) and corresponding solvent control (1%) in the same manner. $GI_{50}$ and $LC_{50}$ values were calculated as previously described (K. D. Paull, E. Hamel, L. Malspeis, In *Cancer Chemotherapeutic Agents*, W. E. Foye, Ed., American Chemical Society, Washington, D.C., 1995, pp. 10-11).

$$GI_{50}: \text{concentration where } 100 \times \frac{(T - T_0)}{(C - T_0)} = 50;$$

$$LC_{50}: \text{concentration where } 100 \times \frac{(T - T_0)}{T_0} = -50.$$

[T=absorbance in treated wells (48 h); $T_0$=absorbance at time zero; C=absorbance in control wells (48 h)]

Example 7

Largazole Activity

Largazole (1) potently inhibited the growth of highly invasive transformed human mammary epithelial cells (MDA-MB-231) in a dose-dependent manner ($GI_{50}$ 8 nM) and induced cytotoxicity at higher concentrations ($LC_{50}$ 117 nM) based on MTT assay. In contrast, nontransformed murine mammary epithelial cells (NMuMG) were significantly less susceptible to compound 1 ($GI_{50}$ 122 nM, $LC_{50}$ 272 nM). Similarly, while fibroblastic osteosarcoma U2OS cells were highly susceptible to largazole (1) with a $GI_{50}$ of 55 nM and $LC_{50}$ of 94 nM, the viability of nontransformed fibroblasts NIH3T3 upon treatment with 1 was significantly less compromised ($GI_{50}$ 480 nM) with no apparent toxicity. The 8- to 15-fold differential growth-inhibitory activity between transformed and nontransformed fibroblasts or epithelial cells, respectively, and selectivity for killing transformed fibroblasts over nontransformed fibroblasts suggests that cancer cells are preferentially targeted by 1. The growth of cancer cell lines derived from colon (HT29) and neuroblastoma (IMR-32) was also strongly inhibited by 1 ($GI_{50}$ values of 12 nM and 16 nM, respectively), accompanied by cytotoxicity ($LC_{50}$ 22 nM for both cell lines).

Largazole (1) also demonstrates remarkable selectivity that is not observed with other validated antitumor natural products tested in parallel. See, e.g., Table 2 re MDA-MB-231/NmuMG cells and U2OS/NIH3T3 cells.

TABLE 2

Growth-inhibitory activity ($GI_{50}$) of natural product drugs

| Compound | MDA-MB-231 | NMuMG | U2OS | NIH3T3 |
|---|---|---|---|---|
| Largazole (1) | 7.7 nM | 122 nM | 55 nM | 480 nM |
| Paclitaxel | 7.0 nM | 5.9 nM | 12 nM | 6.4 nM |
| Actinomycin D | 0.5 nM | 0.3 nM | 0.8 nM | 0.4 nM |
| Doxorubicin | 310 nM | 63 nM | 220 nM | 47 nM |

Example 8

HDAC Inhibition

To test this hypothesis we determined the cellular HDAC activity upon treatment with largazole in HCT-116 cells found to possess high intrinsic HDAC activity. We co-incubated a cell-permeable fluorogenic artificial HDAC substrate (fluor de Lys™, BIOMOL) and largazole (1) and determined that largazole treatment for 8 h resulted in a decrease of HDAC activity in a dose-response manner (FIG. 2a) and, importantly, the $IC_{50}$ for HDAC inhibition closely corresponded with the $GI_{50}$ of largazole in this cell line (FIG. 2a, Table 3). This correlation suggested that HDAC is the relevant target responsible for largazole's antiproliferative effect. Confirmatory, immunoblot analysis of an endogenous HDAC substrate, acetylated histone H3, revealed the same dose-response relationship (FIG. 2b).

Largazole (1) inhibited HDAC activity from a HeLa cell nuclear protein extract rich in class I HDACs 1, 2, and 3 (BIOMOL); however, it is possible that the thioester is cleaved under assay conditions. To investigate that thiol 9 is a reactive species, we liberated 9 from the acetyl analog 8 of largazole (1) and measured enzymatic activity directly; thiol 9 inhibited the HDACs in the nuclear extract of HeLa cells with a similar $IC_{50}$ value (Table 3). Largazole (1) and thiol 9 exhibited similar cellular activity against HDACs derived from nuclear HeLa extracts as well as antiproliferative activity.

TABLE 3

$IC_{50}$ and $GI_{50}$ Values for HDAC and Growth Inhibition (nM)

| | HCT-116 growth inhibition | HCT-116 HDAC cellular assay | HeLa nuclear extract HDACs |
|---|---|---|---|
| 1 | 44 ± 10 | 51 ± 3 | 37 ± 11 |
| 8 | 33 ± 2 | 50 ± 18 | 52 ± 27 |
| 9 | 38 ± 5 | 209 ± 15 | 42 ± 29 |

In Vitro Cellular HDAC Activity Assay.

HCT-116 cells are seeded in 100 µL of medium per well at a density of 3.5×10³ cells/well and grown for 24 h in a sterile 96-well solid bottom plate. The assay is carried out according to the manufacturer's instructions (BIOMOL). Briefly, after 24 h the medium iss replaced with 50 µL/well of medium containing 200 µM fluor de Lys™ substrate and 1 µM of trichostatin A (positive control) and test compounds (largazole, acetyl derivative) ranging from 1 µM to 3.2 nM (Ig/2-fold dilutions) and thiol compound ranging from 10 µM to 300 pM. Plates are incubated at 37° C. for 8 h. After the treatment time, 50 µL per well of 1× fluor de Lys™ Developer containing TSA at 2 µM iss added. After developer addition, plates are incubated for 15 min at 37° C. and fluorescence is read (Ex 360 nm, Em 460 nm).

Immunoblot Analysis.

HCT-116 cells (650,000 cells/dish) are seeded in 10-cm dishes and 24 h later treated with various concentrations of largazole, trichostatin or solvent controls (EtOH for largazole and DMSO for trichostatin). Following incubation for 8 h, whole-cell lysates are prepared using PhosphoSafe lysis buffer (Novagen), proteins extracted, and protein concentration measured using the BCA method (Pierce). Cell lysates containing equal amounts of protein are separated by SDS-PAGE, transferred to PVDF membranes, probed with antibodies and detected with the Supersignal Femto Western blotting kit (Pierce). Anti-acetyl-histone H3 (Lys9/18) and anti-histone H3 primary antibodies are obtained from Millipore and horseradish peroxidase conjugated anti-rabbit secondary antibody is purchased from Cell Signaling.

Cell-Free Enzymatic Assay.

Assay buffer (25 ul in blank and 10 ul in control), 1 µM triehostatin and test inhibitors (ranging from 10 µM to 300 pM) are added to test sample wells of the microtiter plate. HDAC-enriched nuclear protein extract from HeLa cells (BIOMOL) (5 µg in 15 uL) is added to all wells except in the no-enzyme control. The assay plate is equilibrated at 37° C., and then 25 µl of substrate fluor de Lys™ substrate is added to a final concentration of 116 µM. HDAC reaction is allowed to proceed for 15 min and then stopped by addition of 50 µl per well of 1× fluor de Lys™ Developer containing TSA at 2 µM. After developer addition, plates are incubated for 15 min at 37° C. and fluorescence is read (Ex 360 nm, Em 460 nm).
HDAC Assay Using Purified Enzymes.

Similarly as above using HeLa nuclear extract as a source of HDAC activity, the assays can be executed using different pure HDACs of class I and class II to assess specificity.
Cell Differentiation/Dedifferentiation/Transdifferetiation Assays.

The compounds herein are assessed for their ability to induce cell differentiation/dedifferentiation/transdifferentiation by subjecting them to assay conditions essentially as described in protocols known in the art, including for example, as those described in Wu et al. J. Am. Chem. Soc. 2002, 124, 14520-14521; Ding et al. Proc. Natl. Acad. Sci. USA, 2003, 100, 7632-7637; and Chen et al. J. Am. Chem. Soc. 2004, 126, 410-411.

REFERENCES (1) (a) Koehn, F. E.; Carter, G. T. Nat. Rev. Drug Discov. 2005, 4, 206-220. (b) Paterson, I.; Anderson, E. A. Science 2005, 310, 451-453.
(2) Fenical, W.; Jensen, P. R. Nat. Chem. Biol. 2006, 2, 666-673.
(3) Gerwick, W. H.; Tan, L. T.; Sitachitta, N. Alkaloids Chem. Biol. 2001, 57, 75-184.
(4) Luesch, H.; Moore, R. E.; Paul, V. J.; Mooberry, S. L.; Corbett, T. H. J. Nat. Prod 2001, 64, 907-910.
(5) (a) Gerwick, W. H.; Protean, P. J.; Nagle, D. G.; Hamel, E.; Blokhin, A.; Slate, D. L. J. Org. Chem. 1994, 59, 1243-1245. (b) Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. Mol. Pharmacol. 1998, 53, 62-76.
(6) (a) Luesch, H.; Yoshida, W. Y.; Moore, R. E.; Paul, V. J.; Corbett, T. H. J. Am. Chem. Soc. 2001, 123, 5418-5423. (b) Luesch, H.; Chanda, S. K.; Raya, M. R.; DeJesus, P. D.; Orth, A. P.; Walker, J. R.; Izpisúa Belmonte, J. C.; Schultz, P. G. Nat. Chem. Biol. 2006, 2,158-167.
(7) (a) Carmeli, S.; Moore, R. E.; Patterson, G. M. L. Tetrahedron Lett. 1991, 32, 2593-2596. (b) Pattenden, G.; Thom, S. M. J. Chem. Soc. Perkin Trans. I 1993, 1629-1636. (c) Boyce, R. J.; Pattenden, G. Tetrahedron 1995, 51, 7313-7320.
(8) Carmeli, S.; Moore, R. E.; Patterson, G. M. L. J. Am. Chem. Soc. 1990, 112, 8195-8197.
(9) Horton, P.; Inman, W. D.; Crews, P. J. Nat. Prod. 1990, 53, 143-151.
(10) (a) Roller, P.; Au, K.; Moore, R. E. Chem. Commun. 1971, 503-504. (b) Sata, N.; Abinsay, H.; Yoshida, W. Y.; Horgen, F. D.; Sitachitta, N.; Kelly, M.; Scheuer, P. J. J. Nat. Prod. 2005, 68, 1400-1403.
(11) (a) Perez Baz, J.; Cañedo, L. M.; Fernández, Puentes, J. L.; Silva Elipe, M. V. J. Antibiot. (Tokyo) 1997, 50, 738-741. (b) Boger, D. G.; Ichikawa, S. J. Am. Chem. Soc. 2000, 122, 2956-2957.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A method of treating a subject suffering from a cell proliferation related disorder or disease, wherein the subject has been identified as in need of treatment for a cell proliferation related disorder or disease, comprising administering to said subject in need thereof; an effective amount of a compound or pharmaceutical composition of formula I, such that said subject is treated for said disorder:

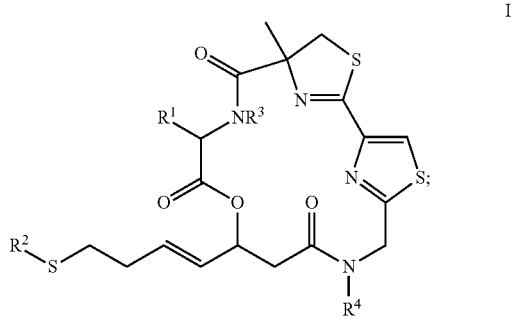

wherein:
each R is independently H or optionally substituted alkyl;
each $R^1$ is independently or optionally substituted alkyl;
each $R^2$ is independently H, optionally substituted alkyl, or C(O)R;
each $R^3$ is independently H, optionally substituted alkyl, C(O)OR, or C(O)NRR;
each $R^4$ is independently H, optionally substituted alkyl, C(O)OR, or C(O)NRR;
the disorder is selected from one or more of the group consisting of brain cancer, mesothelioma, kidney cancer, bladder cancer, prostate cancer, cutaneous T-cell lymphoma, an angiogenesis disorder, and ovarian cancer;
and pharmaceutically acceptable salts thereof.

2. The method of claim 1, wherein the compound of formula I is one of Compounds 1-8.

3. The method of claim 1, wherein the disorder is an angiogenesis disorder.

4. The method of claim 1, wherein the subject is a mammal.

5. The method of claim 1 wherein the subject is a primate or human.

6. The method of claim 1, wherein the compound of formula I is administered intravenously, intramuscularly, subcutaneously, intracerebroventricularly, orally or topically.

7. The method of claim 1, wherein the compound of formula I is administered alone or in combination with one or more other therapeutics.

8. The method of claim 7, wherein the additional therapeutic agent is an anti-cancer agent, chemotherapeutic agent, an anti-angiogenesis agent, cytotoxic agent, or an anti-proliferation agent.

9. A method of treating an histone deacetylase (HDAC) mediated disease or disorder, comprising administering to said subject in need thereof, an effective amount of any of Compounds 1-8, and pharmaceutically acceptable salts thereof;
  wherein the disorder is selected from one or more of the group consisting of brain cancer, mesothelioma, kidney cancer, bladder cancer, prostate cancer, cutaneous T-cell lymphoma, an angiogenesis disorder, and ovarian cancer.

10. A method for treating memory loss, inducing neurogenesis, enhancing memory retention, enhancing memory formation, increasing synaptic potential or transmission, or increasing long term potentiation (LIP) in a subject, comprising administering to said subject in need thereof, an effective amount of a compound of formula (I) in claim 1, or pharmaceutically acceptable salts thereof:

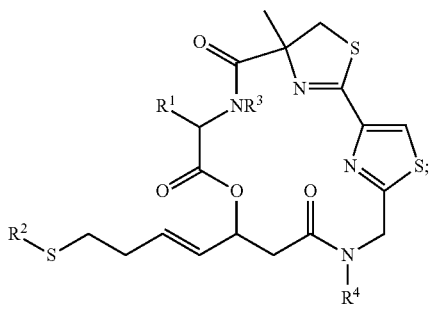

I wherein:
  each R is independently H or optionally substituted alkyl;
  each $R^1$ is independently H, or optionally substituted alkyl;
  each $R^2$ is independently H, optionally substituted alkyl, or C(O)R;
  each $R^3$ is independently H, optionally substituted alkyl, C(O)OR, or C(O)NRR;
  each $R^4$ is independently H, optionally substituted alkyl, C(O)OR, or C(O)NRR.

11. A method for treating diseases and disorders associated with stem cell fate and that are affected by cell differentiation, dedifferentiation or transdifferentiation in a subject, comprising administering to said subject in need thereof, an effective amount of a compound of formula (I) in claim 1, or pharmaceutically acceptable salts thereof:

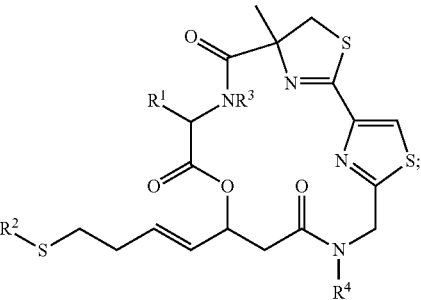

I wherein:
  each R is independently H or optionally substituted alkyl;
  each $R^1$ is independently H, or optionally substituted alkyl;
  each $R^2$ is independently H, optionally substituted alkyl, or C(O)R;
  each $R^3$ is independently H, optionally substituted alkyl, C(O)OR, or C(O)NRR;
  each $R^4$ is independently H, optionally substituted alkyl, C(O)OR, or C(O)NRR.

12. The method of claim 1, wherein $R^3$ and $R^4$ are H.
13. The method of claim 1, $R^1$ is isopropyl.
14. The method of claim 1, wherein the compound is largazole.
15. The method of claim 1, wherein $R^2$ is alkyl.
16. The method of claim 1, wherein $R^2$ is alkylC(O)—.

* * * * *